US008785883B2

(12) United States Patent
Nakazawa et al.

(10) Patent No.: US 8,785,883 B2
(45) Date of Patent: Jul. 22, 2014

(54) TRANSMISSION ELECTRON MICROSCOPE, AND METHOD OF OBSERVING SPECIMEN

(75) Inventors: Eiko Nakazawa, Mito (JP); Hiroyuki Kobayashi, Mito (JP); Susumu Kuwabata, Ibaragi (JP)

(73) Assignee: Hitachi High-Technologies Corporation, Tokyo (JP)

( * ) Notice: Subject to any disclaimer, the term of this patent is extended or adjusted under 35 U.S.C. 154(b) by 299 days.

(21) Appl. No.: 12/918,619

(22) PCT Filed: Apr. 27, 2009

(86) PCT No.: PCT/JP2009/058261
§ 371 (c)(1),
(2), (4) Date: Nov. 19, 2010

(87) PCT Pub. No.: WO2009/133842
PCT Pub. Date: Nov. 5, 2009

(65) Prior Publication Data
US 2011/0057100 A1 Mar. 10, 2011

(30) Foreign Application Priority Data
Apr. 28, 2008 (JP) ................. 2008-117547

(51) Int. Cl.
*G01N 23/00* (2006.01)
*G21K 5/08* (2006.01)
*H01J 37/26* (2006.01)
*H01J 37/30* (2006.01)

(52) U.S. Cl.
CPC ............ *H01J 37/26* (2013.01); *H01J 37/3007* (2013.01)
USPC ...... 250/440.11; 250/306; 250/307; 250/310; 250/311

(58) Field of Classification Search
CPC .......................... H01J 37/3007; H01J 49/0431
USPC ............ 250/306, 307, 309, 310, 311, 440.11, 250/441.11, 443.1
See application file for complete search history.

(56) References Cited

U.S. PATENT DOCUMENTS 5,406,087 A 4/1995 Fujiyoshi et al.
7,304,313 B2 12/2007 Moses et al.
(Continued)

FOREIGN PATENT DOCUMENTS

EP 1 803 141 A1 7/2007
EP 1 868 225 A1 12/2007
(Continued)

OTHER PUBLICATIONS

International Search Report dated Jul. 21, 2009 including English-language translation (Eight (8) pages).
(Continued)

*Primary Examiner* — Nicole Ippolito
*Assistant Examiner* — Hanway Chang
(74) *Attorney, Agent, or Firm* — Crowell & Moring LLP (57) ABSTRACT

Provided is means which enables observation of the shape of a specimen as it is without deforming the specimen. Observation is made by allowing a specimen-holding member having an opening (for example, microgrid and mesh) to hold an ionic liquid and charging a specimen thereto, to allow the specimen to suspend in the ionic liquid. Furthermore, in the proximity of the specimen-holding member, a mechanism of injecting an ionic liquid (ionic liquid introduction mechanism) and/or an electrode are provided. When a voltage is applied to the electrode, the specimen moves or deforms in the ionic liquid. How the specimen moves or deforms can be observed. Furthermore, in the proximity of specimen-holding member, an evaporation apparatus is provided to enable charge of the specimen into the ionic liquid while evaporating. Furthermore, in the proximity of the specimen-holding member, a microcapillary is provided to charge a liquid-state specimen into the ionic liquid. Note that the specimen-holding member is designed to be rotatable.

16 Claims, 9 Drawing Sheets

(56) References Cited

U.S. PATENT DOCUMENTS

| | | |
|---|---|---|
| 7,554,099 B2 | 6/2009 | Chao et al. |
| 2007/0145268 A1 | 6/2007 | Chao et al. |
| 2008/0296516 A1* | 12/2008 | Tomimatsu et al. ..... 250/492.21 |
| 2009/0173882 A1* | 7/2009 | Kuwabata et al. ............ 250/307 |

FOREIGN PATENT DOCUMENTS

| | | |
|---|---|---|
| EP | 1 978 355 A1 | 10/2008 |
| JP | 10-247467 A | 9/1998 |
| JP | 11-30575 A | 2/1999 |
| JP | 2005-108743 A | 4/2005 |
| JP | 2005-174808 A | 6/2005 |
| JP | 2005-529340 A | 9/2005 |
| JP | 2007-165283 A | 6/2007 |
| WO | WO 2006/031104 A1 | 3/2006 |
| WO | WO 2007/083756 A1 | 7/2007 |

OTHER PUBLICATIONS

Form PCT/ISA/237 dated Jul. 21, 2009 (Five (5) pages).

Japanese-language Office Action dated Dec. 11, 2012 (three (3) pages).

Yoshida et al., "In-situ High-Resolution Transmission Electron Microscopy of Liquid Phase Photocatalytic Reaction that uses Excited Electrons by Ionic Liquid", Microscopy and Microanalysis, vol. 13 No. S02, Aug. 1, 2007 XP055106079 pp. 982-983.

Okazaki et al., "Single-step synthesis of gold-silver alloy nanoparticles in ionic liquids by a sputter deposition technique", Chemical Communications, No. 6, Jan. 1, 2008, XP055106544, pp. 691-693.

Extended European search Report dated Mar. 25, 2014, (four (4) pages).

\* cited by examiner

Specimen rotation direction (c)

TRANSMISSION ELECTRON MICROSCOPE, AND METHOD OF OBSERVING SPECIMEN

TECHNICAL FIELD

The present invention relates to a transmission electron microscope and a method for observing a specimen.

BACKGROUND ART

When a specimen is observed by a transmission electron microscope, a specimen to be observed is spread by use of a dispersion medium, such as water and an alcohol on a plastic support film such as a collodion film.

Conventional pretreatment methods for a specimen to be subjected to observation and specimen holding methods are as follows. For example, as shown in Patent Document 1, to observe a scanned electron microscopic image in a wet environment, there is a method of providing a partition to a specimen holding unit to prevent breakage of the specimen and controlling application of pressure. Furthermore, as shown in Patent Document 2, in a process of reducing the thickness of a powder specimen by a FIB process, there is a method of providing a recess in a plate-form specimen-holding substrate, thereby reducing the amount of embedding agent for holding the specimen and reducing the FIB process time. Moreover, as shown in Patent Document 3, when a powder specimen is observed by a transmission electron microscope, there is a method of sprinkling the powder specimen by means of vibration of a vibrator such that the specimen is sufficiently dispersed and deposited onto a collodion film.

[Patent Document 1] JP Patent Publication (Kohyo) No. 2005-529340A
[Patent Document 2] JP Patent Publication (Kokai) No. 11-30575A (1999)
[Patent Document 3] JP Patent Publication (Kokai) No. 49-103565A (1974)

DISCLOSURE OF THE INVENTION

Problems to be Solved by the Invention

However, in any one of the methods of Patent Documents, deformation of a specimen cannot be avoided and a specimen in motion cannot be observed.

To describe more specifically, a support film is a thin organic polymer film sufficient to allow an electron beam to pass; however, it is a solid. Therefore, a specimen placed on the film deforms by its weight or deforms during a drying process before it is set in an electron microscope, with the result that a correct shape of the specimen cannot be observed.

Furthermore, since the interior of an electron microscope is maintained in vacuum, a specimen to be observed must be dried such that it can be observed under vacuum. Therefore, a specimen containing water, such as a biological specimen, is dewatered by use of an organic solvent such as an alcohol before it is set within the microscope. However, denaturation and deformation occur at that time. Thus, it is impossible to observe a shape thereof as close as an original shape present in nature.

Moreover, in the case of a micro-particulate specimen such as an extracted virus or a protein particle, sometimes, the specimen is momentarily frozen, embedded in amorphous ice and subjected to observation. However, since the specimen is embedded in solid ice, movement of the specimen cannot be observed.

The shape of a specimen and the function thereof are closely related with each other. Therefore, to elucidate the function of the specimen, the shape as is in nature is preferably observed. Accordingly, it has been desired to develop an observation method for a specimen without deformation.

The present invention was made in the above circumstances and provides means which enables observation of a natural shape of a specimen without deformation.

Means for Solving the Problems

To solve the problem, in the present invention, an ionic liquid is held in a specimen-holding member having an opening (for example, a microgrid and a mesh) and a specimen is charged to the ionic liquid to allow a specimen to suspend and then observed. Furthermore, in the proximity of the specimen-holding member, a mechanism of injecting an ionic liquid (an ionic-liquid introduction mechanism) and/or an electrode are provided. When a voltage is applied to the electrode, the specimen moves and deforms in the ionic liquid. In this manner, how a specimen moves and deforms can be observed. Furthermore, in the proximity of the specimen-holding member, an evaporation apparatus is provided to charge a specimen into the ionic liquid while evaporating. Moreover, in the proximity of the specimen-holding member, a microcapillary is provided to charge a liquid-state specimen into the ionic liquid. Note that the specimen-holding member is designed to be rotatable.

More specifically, in a transmission electron microscope according to the present invention, an electron beam is applied to a specimen set in a specimen chamber and an image of the specimen is formed from the electron beam transmitted through the specimen. The transmission electron microscope has a specimen holder and an image forming unit for forming a specimen image based on the electron beam transmitted through the specimen. The specimen holder herein is used for introducing a specimen into a specimen chamber. The tip portion thereof, i.e., a specimen-holding member, has an opening for transmitting an electron beam and holding the ionic liquid having a specimen charged. A specimen is introduced into the opening of the specimen-holding member by a liquid introduction mechanism for introducing an ionic liquid. Note that, the amount of ionic liquid to be introduced is controlled by a liquid introduction-amount controlling unit.

A transmission electron microscope according to the present invention further has voltage application means which applies a voltage to a specimen in the ionic liquid held in the opening of the specimen-holding member. Alternatively, the transmission electron microscope may have specimen evaporation means which evaporates a specimen by heating to charge the specimen into an ionic liquid.

The liquid introduction means may be constructed such that any one of a liquid-state specimen, a solution containing a powder specimen dissolved therein and a reagent specimen solution and an ionic liquid are independently introduced into the opening of the specimen-holding member.

The aforementioned transmission electron microscope may be constructed such that a specimen is observed while rotating the specimen-holding member.

The specimen observation method according to the present invention is a method for observing a specimen image by applying an electron beam to a specimen set in a specimen chamber and forming the specimen image from the electron beam transmitted through the specimen. This method includes a step of introducing an ionic liquid having a specimen dispersed therein into the tip portion of a specimen holder, i.e., a specimen-holding member, for introducing the specimen into a specimen chamber, a step of applying an electron beam to an ionic liquid, and a step of observing a specimen image formed based on the electron beam transmitted through the specimen.

In the step of introducing an ionic liquid, the specimen holder is set in the specimen chamber and thereafter the ionic liquid is introduced by use of the liquid introduction mechanism into the opening of the specimen-holding member. At this time, the amount of ionic liquid to be introduced may be controlled by the liquid introduction-amount controlling unit.

The method for observing a specimen further includes a step of applying a voltage to the specimen in an ionic liquid held in the opening of the specimen-holding member.

Note that in the step of introducing an ionic liquid, the ionic liquid may be introduced into the specimen-holding member and subsequently a specimen is heated to evaporate and charged in the ionic liquid.

Furthermore, in the step of introducing an ionic liquid, after the specimen holder is set in the specimen chamber, any one of a liquid-state specimen, a solution containing a powder specimen dissolved therein and a reagent specimen solution and an ionic liquid may be independently introduced into an opening of the specimen-holding member by use of the liquid introduction mechanism.

Furthermore, in the step of applying an electron beam, the electron beam may be applied to a specimen while the specimen-holding member is rotated by use of the specimen-holding member driving mechanism.

Further characteristics of the present invention will be clearly described in Best Mode for Carrying Out of the Invention below and the accompanying drawings.

Advantages of the Invention

According to the present invention, it is possible to observe a natural shape of a specimen without deforming. Note that, when a voltage is applied to a specimen, the specimen in motion or the specimen deformed can be observed.

DESCRIPTION OF SYMBOLS

1 . . . Electron gun, 2 . . . Electron beam, 3a . . . Illumination lens (1), 3b . . . illumination lens (2), 4a . . . Specimen-stage driving mechanism (X direction), 4b . . . Specimen-stage driving mechanism (Y direction), 5 . . . Specimen holder, 6a . . . Objective lens, 6b . . . Intermediate lens, 7 . . . Fluorescent plate, 8 . . . Imaging apparatus such as a CCD camera, 9 . . . Specimen, 10 . . . Liquid vessel, 10a . . . Vessel for ionic liquid, 10b . . . Vessel for reaction solution, 11 . . . Liquid feed pump, 11a . . . Ionic-liquid feed pump, 11b . . . Reaction-solution feed pump, 12 . . . Capillary tube (microcapillary), 12a . . . Capillary tube (microcapillary) for feeding ionic liquid, 12b . . . Capillary tube (microcapillary) for feeding a reaction solution, 13 . . . valve, 13a . . . valve for ionic liquid, 13b . . . valve for reaction solution, 14 . . . liquid-amount controlling unit, 14a . . . Ionic-liquid amount controlling unit, 14b . . . Liquid-amount controlling unit for reaction solution, 15 . . . Power source for motor, 16 . . . Specimen rotation motor, 17 . . . Specimen-holding member, 18 . . . Electrode, 18a . . . Anode, 18b . . . Cathode, 19 . . . Evaporation heater, 20 . . . Voltage application source, 21 . . . Evaporation power source

BEST MODE FOR CARRYING OUT OF THE INVENTION

The present invention relates to a transmission electron microscope by which a specimen allowed to suspend in a liquid can be observed by allowing a specimen holding member to hold an ionic liquid having the specimen charged thereto, and a method for observing a specimen by using the same.

Referring to the accompanying drawings, the embodiments of the present invention will be described below. It should be noted that the each of the embodiments is merely an example of realizing the present invention and will not limit the technical range of the present invention. Furthermore, in the drawings, like reference numerals are used to designate like structural elements.

First Embodiment

Figure 1:
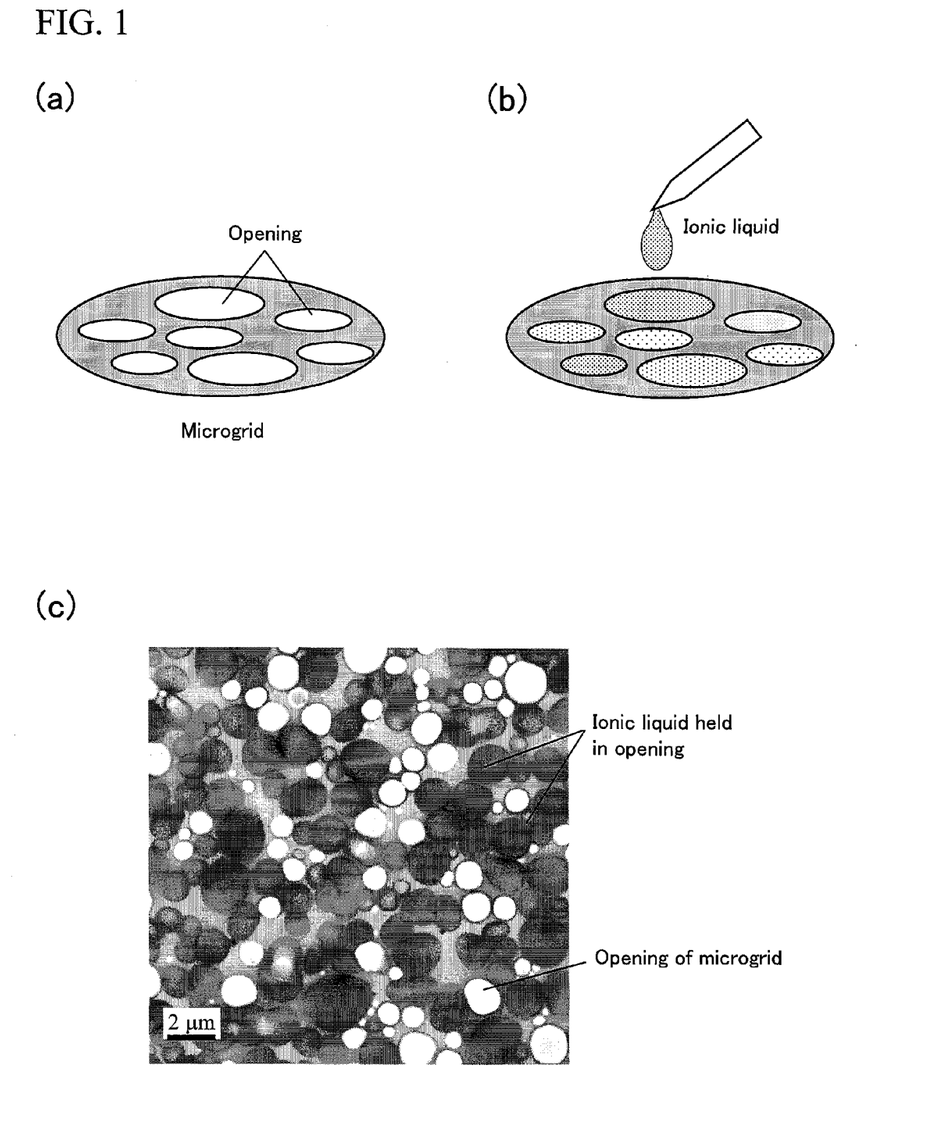
FIG. 1 is a view showing a structure of a specimen-holding member (microgrid) used in each embodiment of the present invention.

FIG. 1 is a view showing a structure of a specimen-holding member (microgrid having a plurality of openings) used in each embodiment of the present invention. FIG. 1 shows a microgrid; however, a member having a plurality of openings, such as a mesh, may be used. In other words, any specimen-holding member may be used as long as it can hold the liquid in the openings with the help of the surface-tension of the liquid when an ionic liquid having a specimen charged thereto is supplied dropwise to the specimen-holding member.

FIG. 1a is a schematic view of a microgrid, which is a specimen-holding member having openings, which hold a specimen to be led in a specimen chamber and through which an electron beam passes. A plurality of openings are formed in a thin film made of an organic polymer, such as a collodion film. FIG. 1b is a schematic view showing an ionic liquid dispersed in the microgrid, more specifically, an ionic liquid dispersed in the openings of the microgrid. Furthermore, FIG. 1c shows a transmission electron image actually observed through a scanning electron microscope by dispersing an ionic liquid in the microgrid. In this figure, an opening of the microgrid holding an ionic liquid and an opening holding no ionic liquid are observed. Note that the ionic liquid used in the present invention is, for example, 1-Butyl-3-methylimidazolium Tetrafluoroborate.

Figure 2:
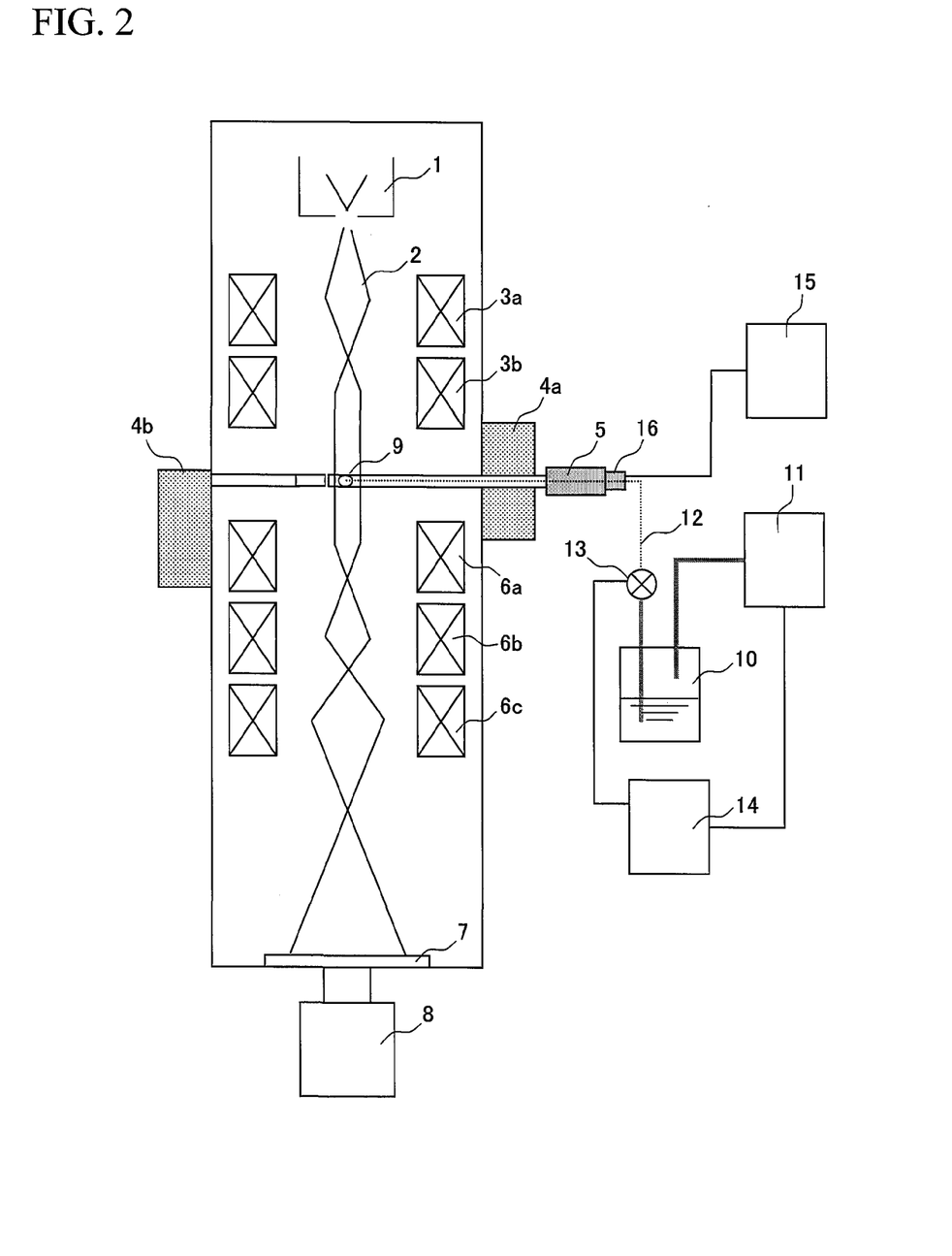
FIG. 2 is a view showing a schematic structure of a transmission electron microscope according to the first embodiment of the invention.

FIG. 2 is a view showing a schematic structure of a transmission electron microscope according to a first embodiment of the invention and equipped with an ionic-liquid injection mechanism. As shown in FIG. 2, an electron beam 2, which is emitted from an electron gun 1 of an electron microscope main body, is applied to specimen 9 held by a specimen holder 5 by an irradiation lens 3a and 3b. Reference numerals 4a and 4b indicate specimen-stage driving mechanisms of the specimen holder 5, which control the driving of the specimen holder 5 in the X-direction and in the Y direction, respectively. The electron beam 3 transmitted though the specimen 9 held by the specimen holder 5 is magnified by a magnification lens system and projected to an imaging apparatus 8 such as a CCD camera. The magnification lens system consists of an objective lens 6a, an intermediate lens 6b and a projection lens 6c. The specimen holder 5 can be rotated by a specimen rotation motor 16 by way of a power source for motor 15.

In the embodiment, a specimen-holding member (the tip portion of the specimen holder 5) 17 is constructed so as to rotate by the specimen-stage driving mechanisms. By virtue of the mechanisms, a specimen is rotated about the optical axis of an electron beam to enable multidirectional observation of the specimen. Furthermore, if serial images are taken while rotating, reconstituted and subjected to electron beam tomography, a three dimensional structure of a specimen can be also observed.

Furthermore, in the embodiment, from the ionic-liquid injection mechanism connected to the specimen holder 5, an ionic liquid is injected into the specimen-holding member 17. The ionic liquid stored in the liquid vessel 10 is injected by a liquid feed pump 11 into the specimen holder 5 through a capillary tube 12. To the capillary tube 12, a valve 13 is provided. By the function of the valve 13, injection of an ionic liquid into the specimen holder 5 is controlled. The driving of the liquid feed pump 11 and the valve 13 is controlled by an ionic-liquid amount controlling unit 14.

Figure 3:
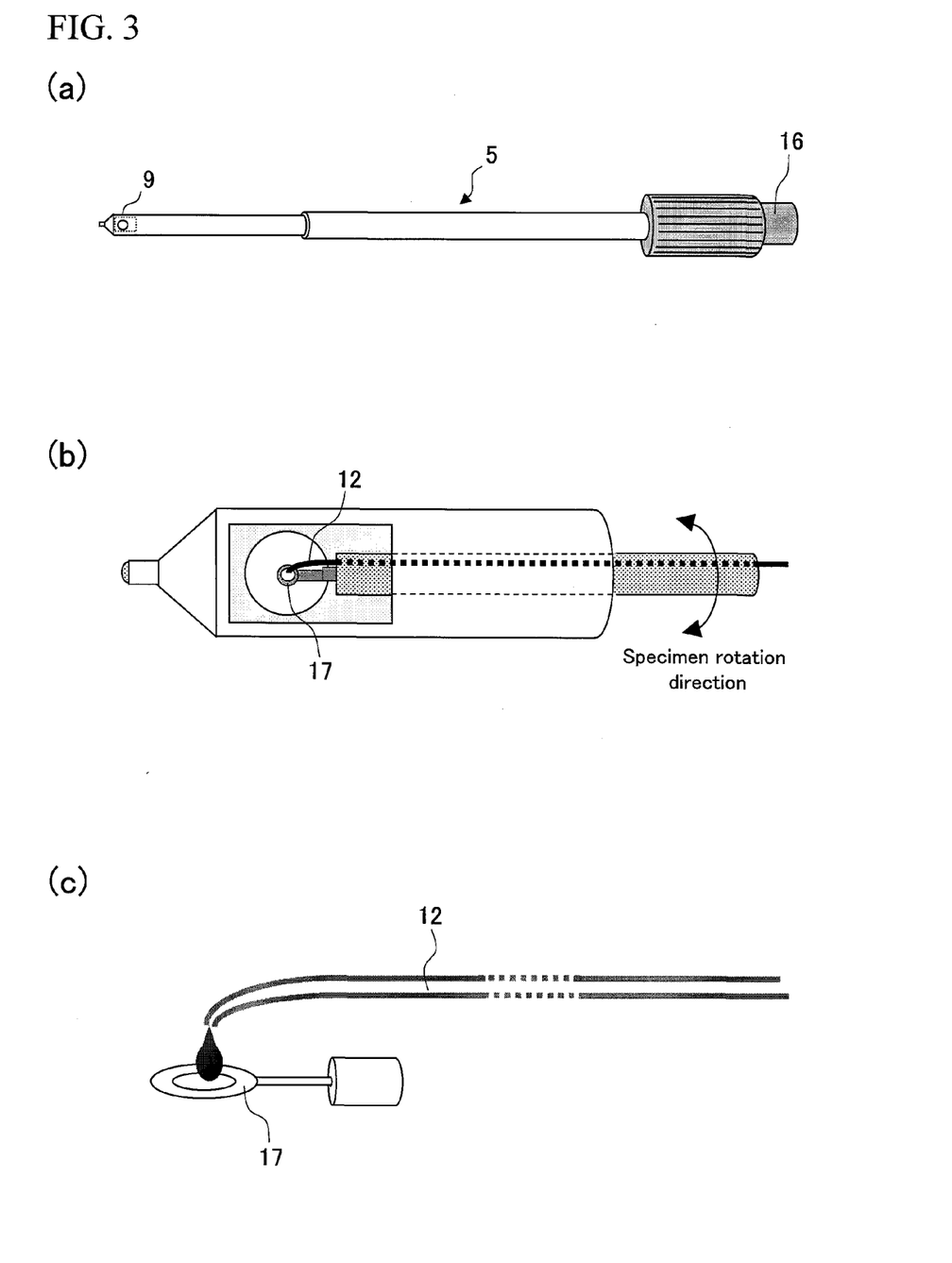
FIG. 3 is a view showing a structure of a specimen holder equipped with an ionic liquid introduction mechanism according to the first embodiment.

FIG. 3 is a view showing a structure of an ionic-liquid injection (introduction) mechanism provided to the specimen holder 5. FIG. 3a shows appearance of the specimen holder 5 having the ionic-liquid injection mechanism. A specimen 9 is placed in the opening of the tip portion. Furthermore, FIG. 3b is an enlarged view of the tip portion of the specimen holder 5. To the specimen-holding member 17, a specimen rotation motor 16 is connected for enabling the specimen-holding member 17 to rotate. Furthermore, as shown in FIG. 3c, an ionic liquid is injected into the specimen-holding member 17 by the capillary tube 12. As the specimen-holding member 17, a thin metal line processed in the form of loop is used, which may be detachably attached like a cartridge.

Note that, in the embodiment, the amount of ionic liquid is controlled to an optimal level sufficient to allow an electron beam to pass while directly observing the dispersion state of the ionic liquid in the specimen-holding member by a transmission electron microscope.

As described above, in the embodiment, since the specimen-holding member 17 can be rotated by the specimen-stage driving mechanisms, a specimen is rotated about the optical axis of an electron beam to enable multidirectional observation of the specimen. Furthermore, if serial images are taken while rotating, reconstituted and subjected to electron beam tomography, a three dimensional structure of a specimen can be also observed.

Second Embodiment

Figure 4:
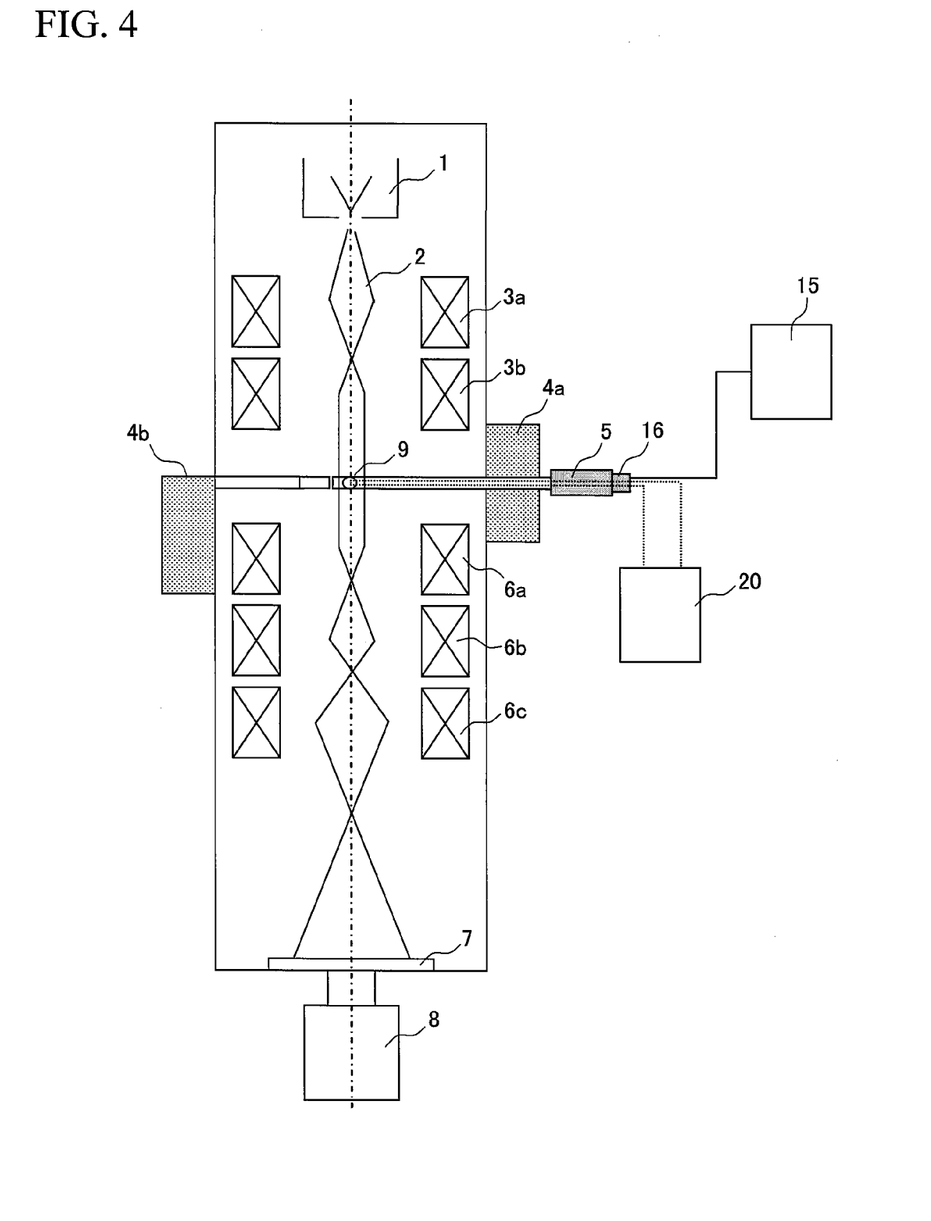
FIG. 4 is a view showing a schematic structure of a transmission electron microscope according to the second embodiment of the invention.

FIG. 4 is a view showing a schematic structure of a transmission electron microscope according to a second embodiment of the invention, which has a specimen holder equipped with an electrode. In this embodiment, unlike the first embodiment, a voltage application source 20, which is connected to a specimen holder 5, is operated to apply a voltage to an ionic liquid. In this manner, an electric field is applied to a specimen 9. Furthermore, although the ionic liquid introduction mechanism of the first embodiment is not shown in FIG. 4, needless to say, the mechanism may be provided.

Figure 5:
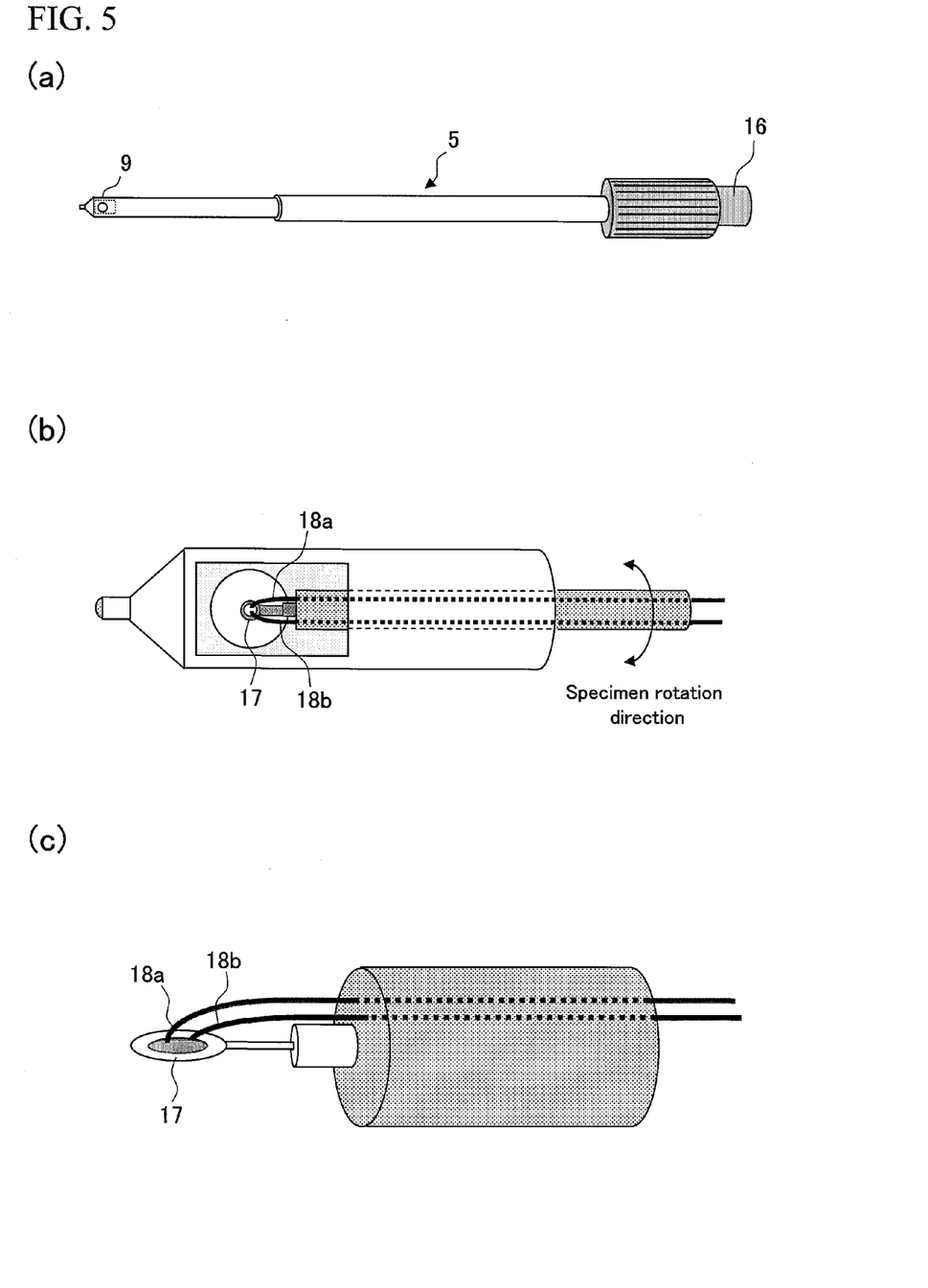
FIG. 5 is a view showing the structure of a specimen holder equipped with an electrode according to the second embodiment.

FIG. 5 is a view showing the structure of the specimen holder 5 equipped with an electrode according to the second embodiment. FIG. 5a shows appearance of the specimen holder 5 equipped with an electrode. A specimen 9 is placed in the opening of the tip portion of the specimen holder 5. FIG. 5b is enlarged view of the tip portion of the specimen holder 5. The tip portion of the specimen holder 5, i.e., a specimen-holding member 17, can be rotated by a specimen rotation motor 16 connected to the member. Furthermore, as shown in FIG. 5c, the specimen-holding member 17 holding an ionic liquid is equipped with an electrode 18.

By virtue of the structure as mentioned above, in the embodiment, a specimen injected in an ionic liquid and dispersed in the specimen-holding member is moved or changed in shape by voltage application. How to move and change can be directly observed by a transmission electron microscope. By use of this, for example, in a semiconductor manufacturing process, how a specimen changes can be checked. Furthermore, in the embodiment, since the specimen-holding member can be rotated by the specimen-stage driving mechanisms, a specimen is rotated about the optical axis of an electron beam to enable multidirectional observation of the specimen. Furthermore, if serial images are taken while rotating, reconstituted and subjected to electron beam tomography, a three dimensional structure of a specimen can be also observed.

Third Embodiment

Figure 6:
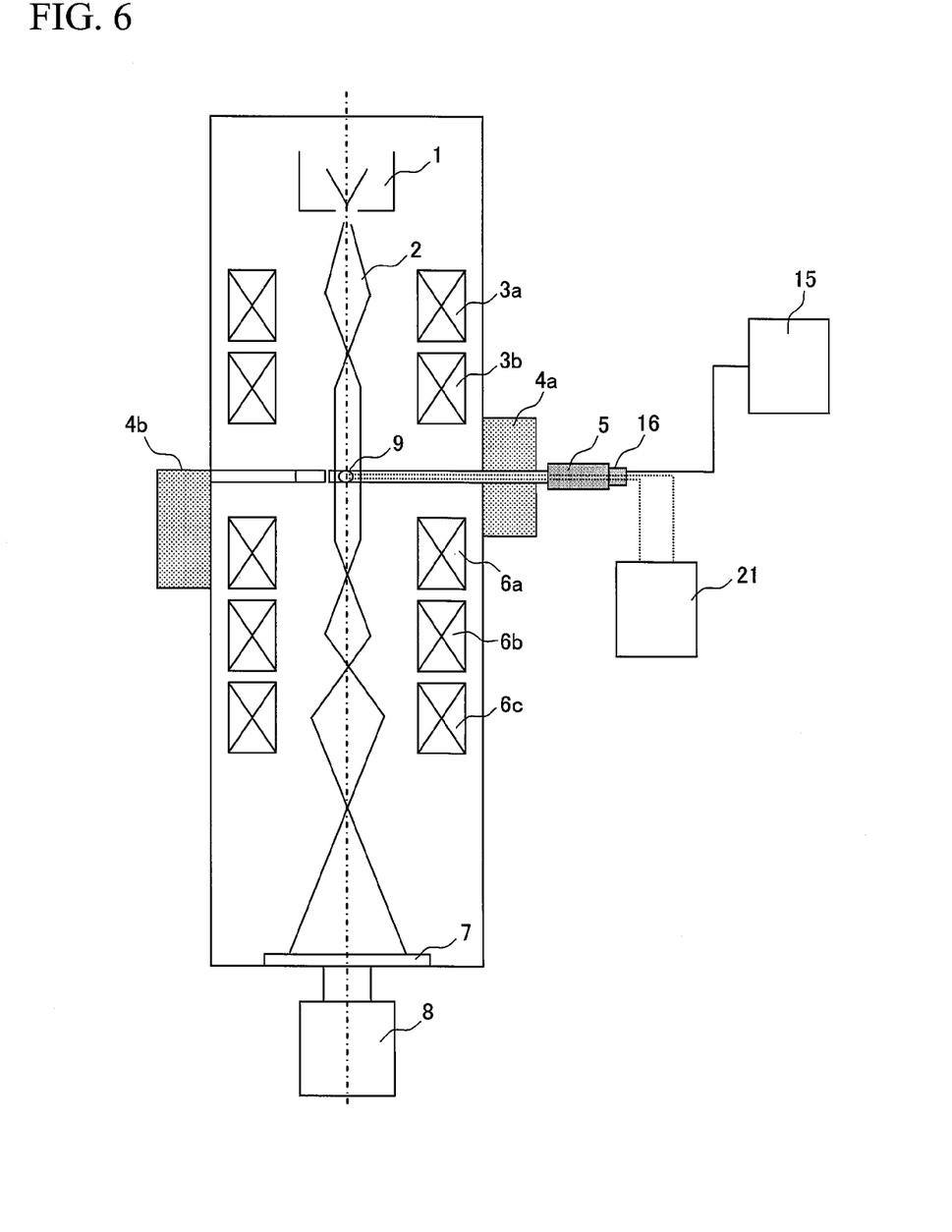
FIG. 6 is a view showing a schematic structure of a transmission electron microscope according to the third embodiment of the invention.

FIG. 6 is a view showing a schematic structure of a transmission electron microscope according to the third embodiment of the invention, which is equipped with a specimen charge mechanism by evaporation.

In the embodiment, unlike from the first embodiment, an evaporation power source 21 is connected to a specimen holder 5 so as to charge a specimen into an ionic liquid by evaporation. Also in this embodiment, the ionic liquid introduction mechanism according to the first embodiment may be provided.

Figure 7:
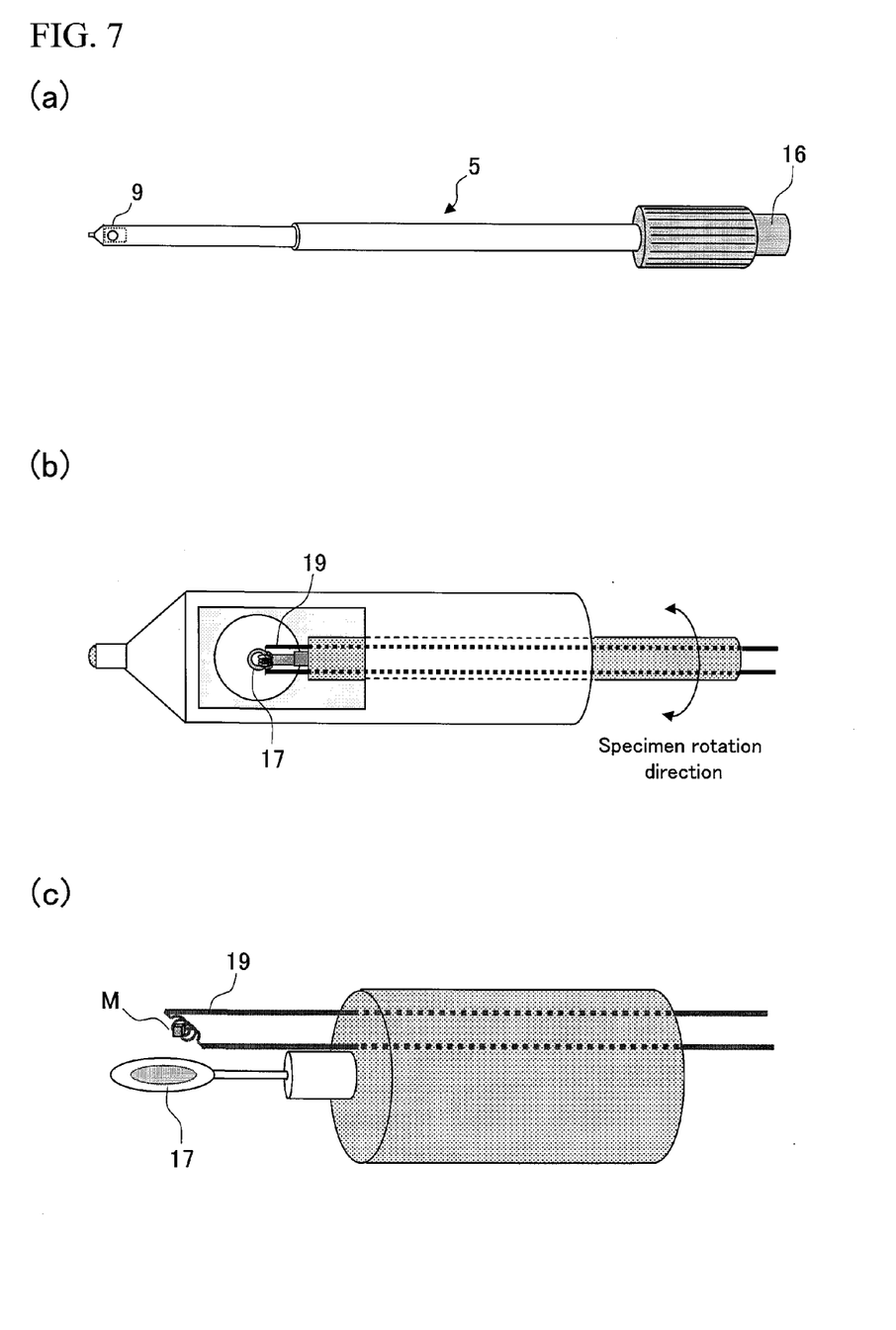
FIG. 7 is a view showing a structure of specimen holder equipped with a specimen charge mechanism by evaporation according to the third embodiment.

FIG. 7 shows a structure of the specimen holder 5 having the specimen charge mechanism by evaporation, according to the third embodiment. FIG. 7a shows appearance of the specimen holder 5 having the specimen charge mechanism by evaporation. A specimen 9 is placed in the opening of the tip portion. FIG. 7b is an enlarged view of the tip portion of the specimen holder 5. The tip portion of the specimen holder 5, i.e., a specimen-holding member 17, can be rotated by a specimen rotation motor 16 connected to the member. Furthermore, as shown in FIG. 7c, an evaporation heater 19 is provided in the proximity of the specimen-holding member 17 holding an ionic liquid. A material to be evaporated set on the evaporation heater 19 such as palladium and platinum (referred to as metal M) is melted on the evaporation heater 19, when heated by supplying a current by the evaporation power source 21 and microparticles thereof are charged into an ionic liquid.

In the embodiment, the shape of evaporated metal microparticles in an ionic liquid and how microparticles are evaporated and charged into an ionic liquid can be directly observed by a transmission electron microscope. By virtue of this, the strength of materials constituting a micro region of a specimen and compatibility between the materials (ions) can be analyzed.

Furthermore, in the embodiment, since the specimen-holding member can be rotated by the specimen-stage driving mechanisms, a specimen is rotated about the optical axis of an electron beam to enable multidirectional observation of the specimen. Furthermore, if serial images are taken while rotating, reconstituted and subjected to electron beam tomography, a three dimensional structure of a specimen can be also observed.

Fourth Embodiment

Figure 8:
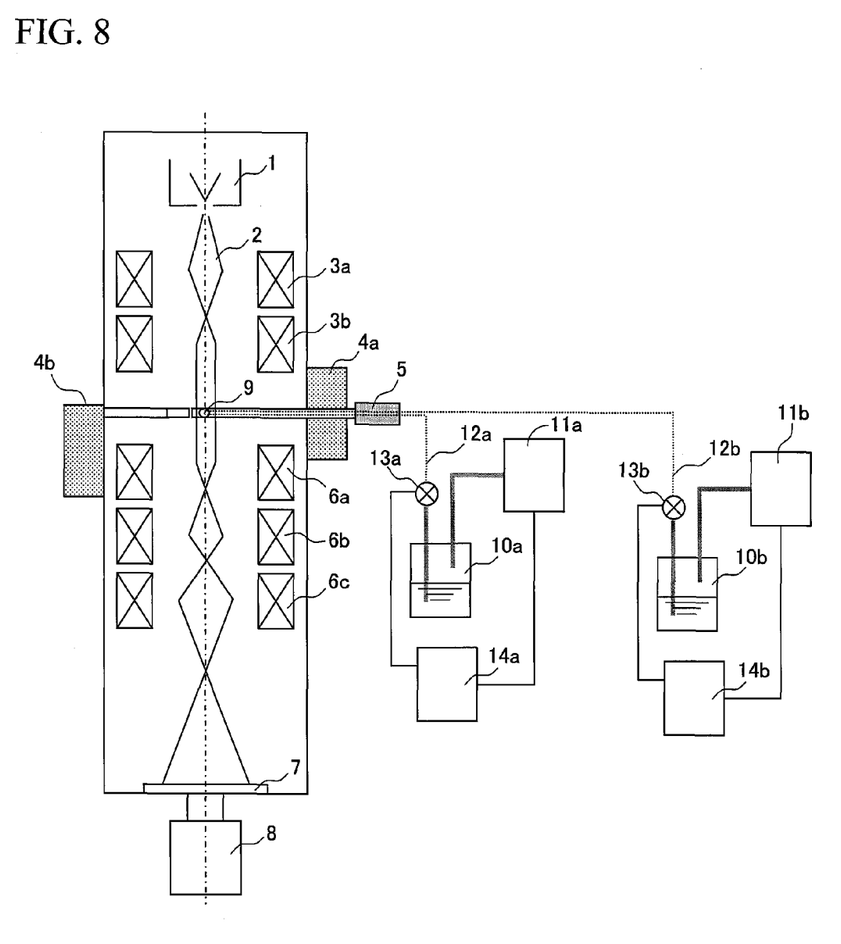
FIG. 8 is a view showing a schematic structure of a transmission electron microscope according to the fourth embodiment of the invention.

FIG. 8 is a view showing a schematic structure of a transmission electron microscope according to a fourth embodiment of the invention, which has an ionic liquid and reaction-solution introduction (injection) mechanisms.

In the embodiment, an ionic liquid and a reaction solution can be injected respectively by independent ionic-liquid and reaction-solution introduction mechanisms connected to a specimen holder 5 while independently controlling the injection amounts. To describe more specifically, the ionic liquid and reaction solution are stored in liquid vessels 10a and 10b, injected into the specimen holder 5 respectively by means of liquid feed pumps 11a and 11b by way of respective capillary tubes (microcapillary) 12a and 12b. To the capillary tubes 12a and 12b respectively feeding an ionic liquid and the reaction solution, valves 13a and 13b are provided respectively. Injection of the ionic liquid and reaction solution to the specimen holder 5 is controlled by the function of the valves 13a and 13b. Driving of the liquid feed pumps 11a and 11b and the valves 13a and 13b is controlled by ionic liquid and reaction-solution amount controlling units 14a and 14b.

Figure 9:
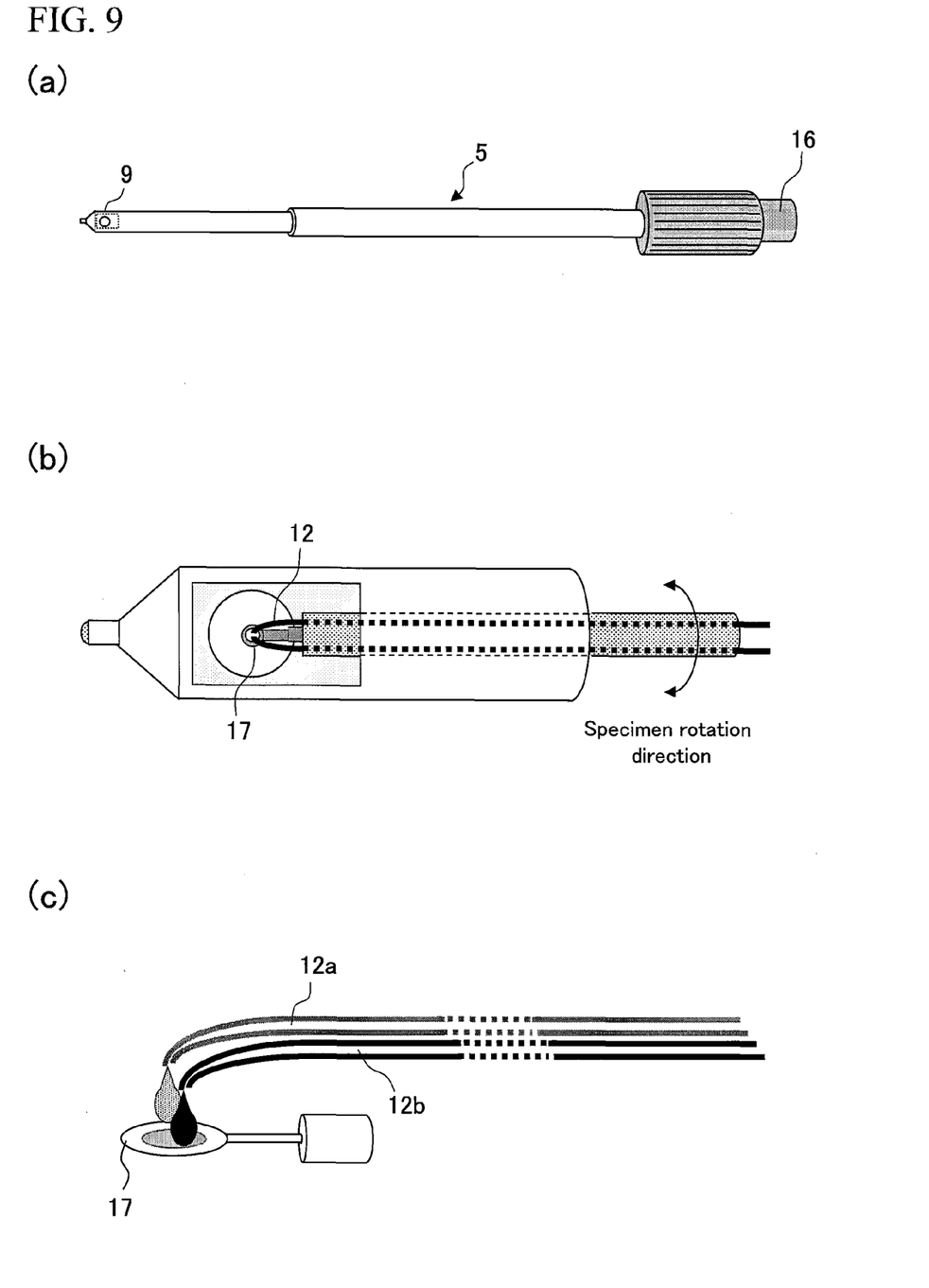
FIG. 9 is a view showing a structure of a specimen holder equipped with an ionic-liquid and reaction-solution introduction mechanism according to the fourth embodiment.

FIG. 9 shows a structure of the specimen holder 5 according to the fourth embodiment, which has ionic liquid and reaction-solution introduction mechanisms. FIG. 9a shows appearance of the specimen holder 5 having the ionic liquid and reaction solution injection mechanisms. A specimen 9 is placed in the opening of the tip portion. FIG. 9b shows an enlarged view of the tip portion of the specimen holder 5. A specimen-holding member 17 can be rotated by a specimen rotation motor 16 connected to the member. Furthermore, as shown in FIG. 9c, the ionic liquid and reaction solution are injected by the respective liquid-feed capillary tubes 12a and 12b into the specimen-holding member 17. As the specimen-holding member 17 herein, a thin metal line processed in the form of loop is used, which may be detachably attached like a cartridge.

In the embodiment, in the proximity of the specimen-holding member, a mechanism for introducing a liquid-state specimen, a solution containing a powder specimen dissolved therein or a reagent solution, for example, a microcapillary, is provided to charge a liquid specimen into an ionic liquid. At this time, if an enzyme is introduced as a specimen, an enzyme reaction can be directly observed by an electron microscope. Alternatively, if a specimen, which is an antibody having an antigen dispersed therein, is introduced, how to react with a reagent, in other words, an antigen-antibody reaction, can be directly observed by an electron microscope. In the embodiment, since the specimen holding member can be rotated by the specimen-stage driving mechanisms, a specimen is rotated about the optical axis of an electron beam to enable multidirectional observation of the specimen. Furthermore, if serial images are taken while rotating, reconstituted and subjected to electron beam tomography, a three dimensional structure of a specimen can be also observed.

<Summary>

According to embodiments of the present invention, in a transmission electron microscope, an ionic liquid is used as a dispersion medium to allow a specimen to suspend therein to observe the specimen without deformation.

Furthermore, a mechanism for injecting an ionic liquid is provided in the proximity of a specimen-holding member. By virtue of this, the injection amount of ionic liquid is controlled. Furthermore, whether the injection amount of ionic liquid is optimum or not can be checked while observing an electron microscopic image. Therefore, the thickness of a film serving as a specimen support film can be controlled without fail.

Furthermore, an electrode is provided in the proximity of a specimen-holding member. By virtue of this, a specimen can be moved by supplying a current, and a phenomenon thereof can be directly observed by an electron microscope.

Furthermore, an evaporation apparatus is provided in the proximity of a specimen-holding member. By virtue of this, metal microparticles are introduced by evaporation in an ionic liquid to allow direct observation of microparticles and evaporation phenomenon by an electron microscope.

A mechanism for introducing a liquid-state specimen, a solution containing a powder specimen dissolved therein or a reagent solution, for example, a microcapillary, is provided in the proximity of a specimen-holding member. By virtue of this, a liquid specimen can be charged into an ionic liquid. At this time, if an enzyme is introduced as a specimen, an enzyme reaction can be directly observed by an electron microscope. Alternatively, if an antibody, in the case of a specimen having an antigen dispersed therein, how to react with the reagent, in other words, an antigen-antibody reaction, can be directly observed by an electron microscope.

Since a specimen holding member can be rotated by specimen-stage driving mechanisms, a specimen is rotated about the optical axis of an electron beam to enable multidirectional observation of the specimen. Furthermore, if serial images are taken while rotating, reconstituted and subjected to electron beam tomography, a three dimensional structure of a specimen can be also observed.

The invention claimed is:

1. A transmission electron microscope in which an electron beam is applied to a specimen set in a specimen chamber and an image of the specimen is formed from the electron beam transmitted through the specimen, the transmission electron microscope comprising:

a specimen holder for introducing the specimen into the specimen chamber, wherein the specimen holder has a specimen-holding member at a tip portion, and the specimen-holding member has an opening for transmitting the electron beam and for holding, entirely by surface tension, an ionic liquid having the specimen charged therein, wherein the ionic liquid fills the entire opening, and an image forming unit for forming an image of the specimen based on the electron beam transmitted through the specimen.

2. The transmission electron microscope according to claim 1, further comprising a liquid introduction mechanism for introducing the ionic liquid into the opening of the specimen-holding member.

3. The transmission electron microscope according to claim 2, further comprising a liquid introduction-amount controlling unit for controlling an introduction amount of the ionic liquid.

4. The transmission electron microscope according to claim 1, further comprising voltage application means which applies a voltage to the specimen in the ionic liquid held in the opening of the specimen-holding member.

5. The transmission electron microscope according to claim 1, further comprising specimen evaporation means which evaporates the specimen by heating and charges the specimen in the ionic liquid.

6. The transmission electron microscope according to claim 1, further comprising a liquid introduction mechanism for independently introducing any one of a liquid-state specimen, a solution containing a powder specimen dissolved therein, or a reagent specimen solution, and the ionic liquid.

7. The transmission electron microscope according to claim 1, further comprising a specimen-holding member driving mechanism for rotating the specimen-holding member.

8. A method for observing a specimen in which an electron beam is applied to a specimen set in a specimen chamber and a specimen image formed from the electron beam transmitted through the specimen is observed, the method comprising:
   a step of introducing an ionic liquid having the specimen dispersed therein into an opening of a specimen-holding member at a tip potion of a specimen holder for introducing the specimen to the specimen chamber, wherein the ionic liquid is held in the opening entirely by surface tension, and the ionic liquid fills the entire opening,
   a step of applying the electron beam to the ionic liquid, and
   a step of observing a specimen image formed based on the electron beam transmitted through the specimen.

9. The method for observing a specimen according to claim 8, wherein, in the step of introducing the ionic liquid, the specimen holder is set in the specimen chamber, and thereafter, the ionic liquid is introduced in the opening of the specimen-holding member by use of a liquid introduction mechanism.

10. The method for observing a specimen according to claim 9, wherein an ionic liquid introduction amount is controlled by a liquid introduction-amount controlling unit.

11. The method for observing a specimen according to claim 8, further comprising the step of applying a voltage to the specimen in the ionic liquid contained in the opening of the specimen-holding member.

12. The method for observing a specimen according to claim 8, wherein, in the step of introducing the ionic liquid, the ionic liquid is introduced into the specimen-holding member and subsequently the specimen is evaporated by heating and charged into the ionic liquid.

13. The method for observing a specimen according to claim 8, wherein, in the step of introducing the ionic liquid, the specimen holder is set in the specimen chamber, and thereafter, any one of a liquid-state specimen, a solution containing a powder specimen dissolved therein, or a reagent specimen solution, and the ionic liquid are independently introduced in the opening of the specimen-holding member by use of the liquid introduction mechanism.

14. The method for observing a specimen according to claim 8, wherein, in the step of applying the electron beam, the electron beam is applied to the specimen while the specimen-holding member is rotated by use of a specimen-holding member driving mechanism.

15. The transmission electron microscope according to claim 1, wherein the specimen-holding member comprises a thin film, and the opening is formed in the thin film.

16. The method for observing a specimen according to claim 8, wherein the specimen-holding member comprises a thin film, and the opening is formed in the thin film.

* * * * *